US008054461B2

(12) United States Patent
Kuo et al.

(10) Patent No.: US 8,054,461 B2
(45) Date of Patent: Nov. 8, 2011

(54) SYSTEMS FOR PERFORMING RAMAN SPECTROSCOPY

(75) Inventors: Huei Pei Kuo, Cupertino, CA (US); Jing Tang, Menlo Park, CA (US); Alexandre M. Bratkovski, Mountain View, CA (US); Theodore I. Kamins, Palo Alto, CA (US); Wei Wu, Mountain View, CA (US); Michael Renne Ty Tan, Menlo Park, CA (US); Shih-Yuan Wang, Palo Alto, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 0 days.

(21) Appl. No.: 12/286,490

(22) Filed: Sep. 30, 2008

(65) Prior Publication Data

US 2010/0079754 A1    Apr. 1, 2010

(51) Int. Cl.
*G01J 3/44* (2006.01)
(52) U.S. Cl. ...................................................... 356/301
(58) Field of Classification Search ................... 356/301
See application file for complete search history.

(56) References Cited

U.S. PATENT DOCUMENTS

| | | | | |
|---|---|---|---|---|
| 4,645,340 | A * | 2/1987 | Graham et al. | 356/301 |
| 5,615,673 | A * | 4/1997 | Berger et al. | 600/326 |
| 6,538,775 | B1 * | 3/2003 | Bowley et al. | 359/3 |
| 2004/0179784 | A1 * | 9/2004 | Vancoille et al. | 385/47 |
| 2005/0084912 | A1 * | 4/2005 | Poponin | 435/7.1 |
| 2009/0009165 | A1 * | 1/2009 | Ichimura et al. | 324/304 |
| 2009/0096995 | A1 * | 4/2009 | Malfait | 353/31 |
| 2009/0103082 | A1 * | 4/2009 | Black et al. | 356/301 |

* cited by examiner

*Primary Examiner* — Tarifur Chowdhury
*Assistant Examiner* — Abdullahi Nur

(57) ABSTRACT

Various embodiments of the present invention relate generally to systems for performing Raman spectroscopy. In one embodiment, a system for performing Raman spectroscopy comprises an analyte holder having a surface configured to retain an analyte and a light concentrator configured to receive an incident beam of light, split the incident beam into one or more beams, and direct the one or more beams to substantially intersect at the surface. The system may also include a collector configured to focus each of the one or more beams onto the surface, collect the Raman scattered light emitted from the analyte, and direct the Raman scattered light away from the surface.

20 Claims, 10 Drawing Sheets

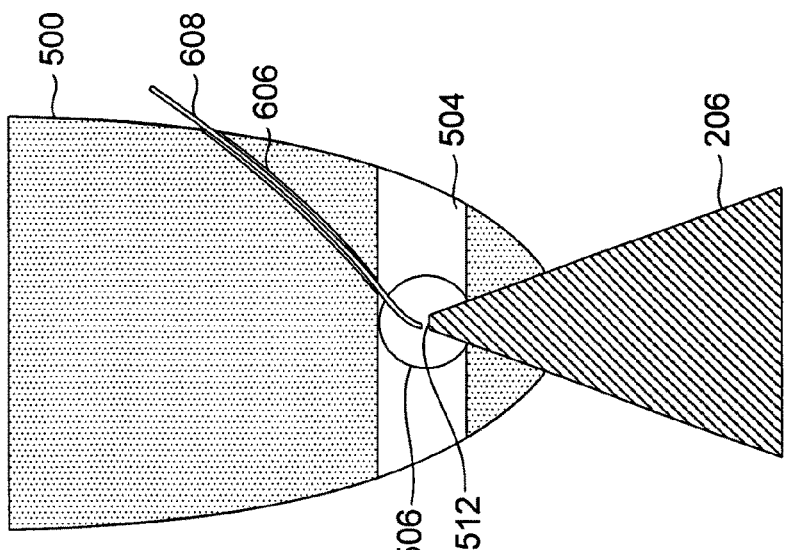
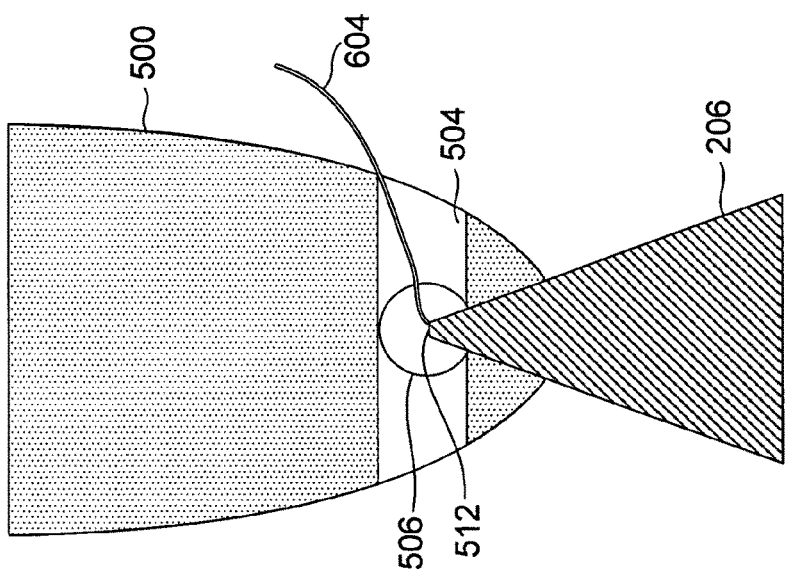
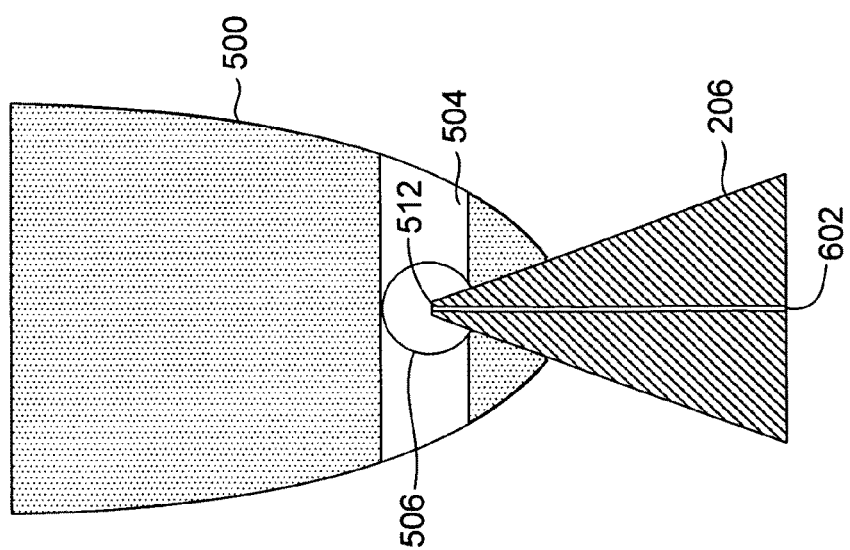

SYSTEMS FOR PERFORMING RAMAN SPECTROSCOPY

TECHNICAL FIELD

Embodiments of the present invention relate generally to systems for performing surface-enhanced Raman spectroscopy.

BACKGROUND

Raman spectroscopy is a spectroscopic technique used in condensed matter physics and chemistry to study vibrational, rotational, and other low-frequency modes of a molecular system. In a Raman spectroscopic experiment, a monochromatic beam of light, typically in the ultraviolet, visible, or infrared regions of the electromagnetic spectrum, passes through a sample of molecules and a spectrum of scattered light is emitted. The term "light" refers to electromagnetic radiation having wavelengths within the visible and non-visible portions of the electromagnetic spectrum, such as the ultraviolet and infrared portions of the spectrum. The spectrum of light emitted from the molecule is called a "Raman spectrum" and the scattered light is also called "Raman scattered light." A Raman spectrum can reveal electronic, vibrational, and rotational energies levels of a molecule. Different molecules produce different Raman spectrums that can be used like a fingerprint to identify molecules and even determine the structure of molecules. For example, Raman gas analyzers have many practical applications such as providing real-time monitoring of molecular changes in gas mixtures.

The Raman scattered light generated by a compound (or ion) adsorbed on or within a few nanometers of a structured metal surface can be $10^3$-$10^6$ or more times greater than the Raman scattered light generated by the same compound in solution. This surface-enhanced Raman scattering ("SERS") is strongest on silver ("Ag"), gold ("Au"), and copper ("Cu") surfaces. SERS arises from two mechanisms. The first mechanism is an enhanced electromagnetic field produced at the surface of a metal. When the wavelength of incident light is close to the plasma wavelength of the metal, conduction electrons in the metal surface are excited into an extended, surface, excited electronic state called a "surface plasmon." Molecules adsorbed or in close proximity to the surface experience a relatively strong electromagnetic field. Molecular vibrational modes directed normal to the surface are most strongly enhanced. The intensity of the surface plasmon resonance is dependent on many factors including the wavelength of the incident light and the morphology of the metal surface. The second mode of enhancement occurs from the formation of a charge-transfer complex between the surface and a molecule absorbed to the surface. The electronic transitions of many charge transfer complexes are typically in the visible range of the electromagnetic spectrum.

SERS is often used to study monolayers of materials adsorbed on metals. However, typical optical systems for performing Raman spectroscopy consist of an optical microscope that focuses light from a source onto an analyte, and the Raman spectrum emitted from the analyte is gathered through the same optical system. Collecting an emission spectrum in this manner is inefficient and these optical systems are often bulky.

SUMMARY

Various embodiments of the present invention relate generally to systems for performing Raman spectroscopy. In one embodiment, a system for performing Raman spectroscopy comprises an analyte holder having a surface configured to retain an analyte and a light concentrator configured to receive an incident beam of light, split the incident beam into one or more beams, and direct the one or more beams to substantially intersect at the surface. The system may also include a collector configured to focus each of the one or more beams onto the surface, collect the Raman scattered light emitted from the analyte, and direct the Raman scattered light away from the surface.

BRIEF DESCRIPTION OF THE DRAWINGS

FIGS. 6A-6C show three cross-sectional views of the analyte holder and the compound parabolic concentrator along a line I-I, shown in FIG. 5B, in accordance with embodiments of the present invention.

DETAILED DESCRIPTION

Embodiments of the present invention relate to systems for performing Raman spectroscopy. The systems can be compact for ease of portability, provide energy efficient utilization of a coherent light source, are configured to exploit the coherency of the light source to obtain enhancement of local electric field interaction with an analyte, and provide efficient collimation and collection of Raman scattered light emitted from the analyte for analysis. Embodiments also include configuring a surface to retain an analyte within regions of the surface where the strength of the enhanced electric field is greatest.

Figure 1A:
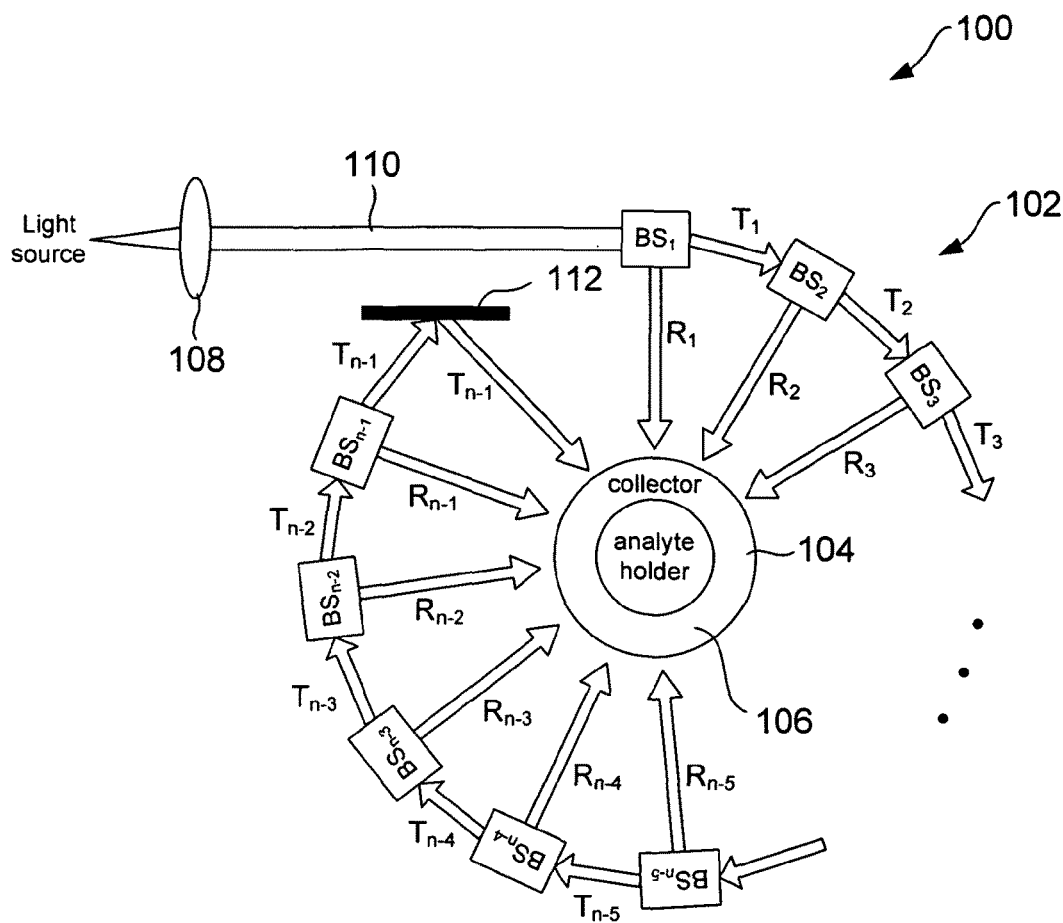
FIGS. 1A-1B show schematic representations of general systems for performing Raman spectroscopy configured in accordance with embodiments of the present invention.
Figure 1B:
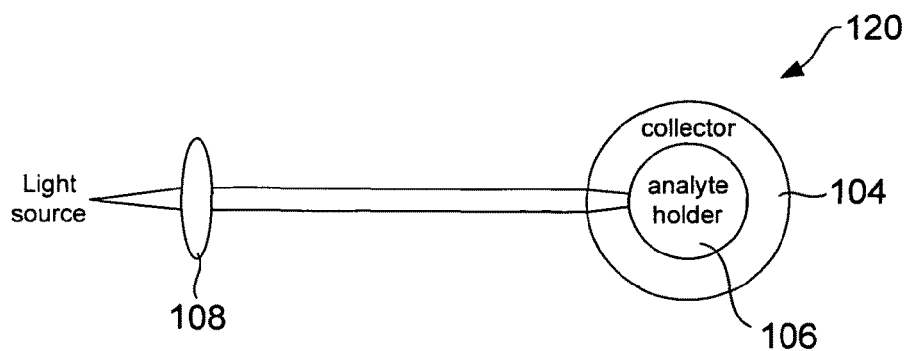

FIGS. 1A-1B show schematic representations of general systems for performing Raman spectroscopy configured in accordance with embodiments of the present invention. In FIG. 1A, a system 100 comprises a light concentrator 102, a collector 104, and an analyte holder 106. A light source outputs light, preferably coherent light, that is collimated by a lens 108 into an incident beam 110 that enters the light concentrator 102. The light concentrator 102, comprises a mirror 112 and n−1 beamsplitters identified as "$BS_m$" where n is a positive-integer and m is a positive integer satisfying $1 \leq m \leq n-1$. The beamsplitters are configured to reflect portions of the incident beam toward the collector 104. Each portion reflected toward the collector 104 is a beam of coherent light having approximately 1/nth of the total power of the incident beam 110. The reflectance and transmittance of the beamsplitters can be approximated as follows. The beamsplitters reflect a fraction of the optical signal power in accordance with:

$$R_m = \frac{1}{(n-m+1)}$$

and transmit a fraction of the optical signal power in accordance with:

$$T_m = \frac{(n-m)}{(n-m+1)}$$

Thus, a beamsplitter $B_m$ receives a beam with optical power P from the light source or an adjacent beamsplitter and outputs a reflected portion with optical power $PR_m$ and outputs a transmitted portion with optical power $PT_m$, where $P = PR_m + PT_m + L_m$, and $L_m$ represents optical power loss at the beamsplitter $BS_m$ due to absorption, scattering, or misalignment.

The analyte holder 106 includes a surface (not shown) that retains an analyte. The collector 104 receives and focuses each of the n reflected beams onto the surface. The analyte in response to the incident light emits a Raman spectrum of Raman scattered light. The surface of the substrate is configured to respond to the wavelength of the focused beams of light by producing surfaces plasmons that further enhance the Raman scattering. The collector 104 gathers and collimates the Raman scattered light and directs the collimated light away from the surface toward a spectrometer (not shown). The Raman spectrum can then be analyzed to determine the structure and identify the molecules present in the analyte. In other embodiments, the beamsplitters $BS_m$ and mirror 112 can be eliminated. In FIG. 1B, rather than splitting the incident beam of light, the collector 104 focuses the incident beam 110 directly onto the surface of the analyte holder 106.

Figure 3:
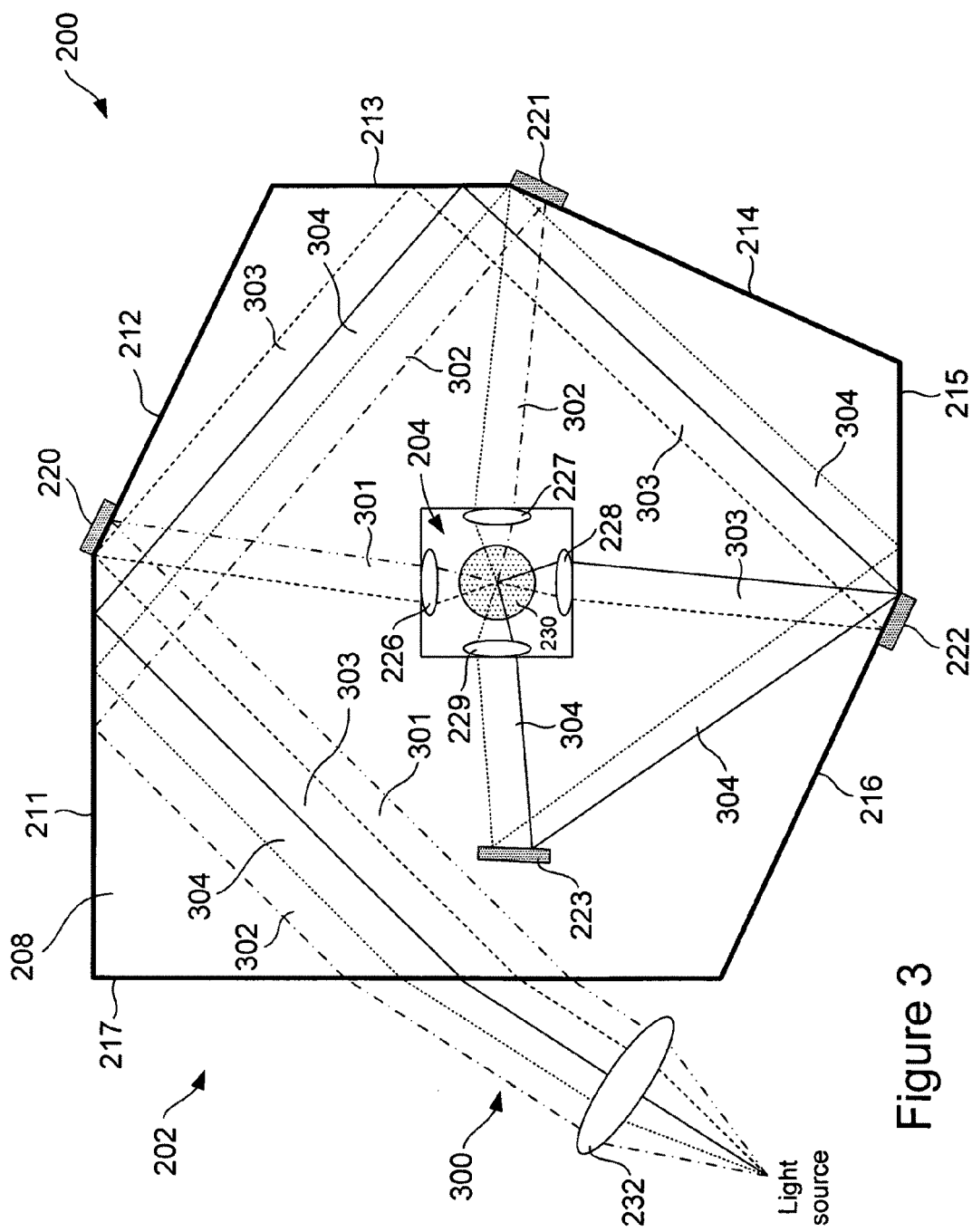
FIG. 3 shows operation of the first system in accordance with embodiments of the present invention.
Figure 4:
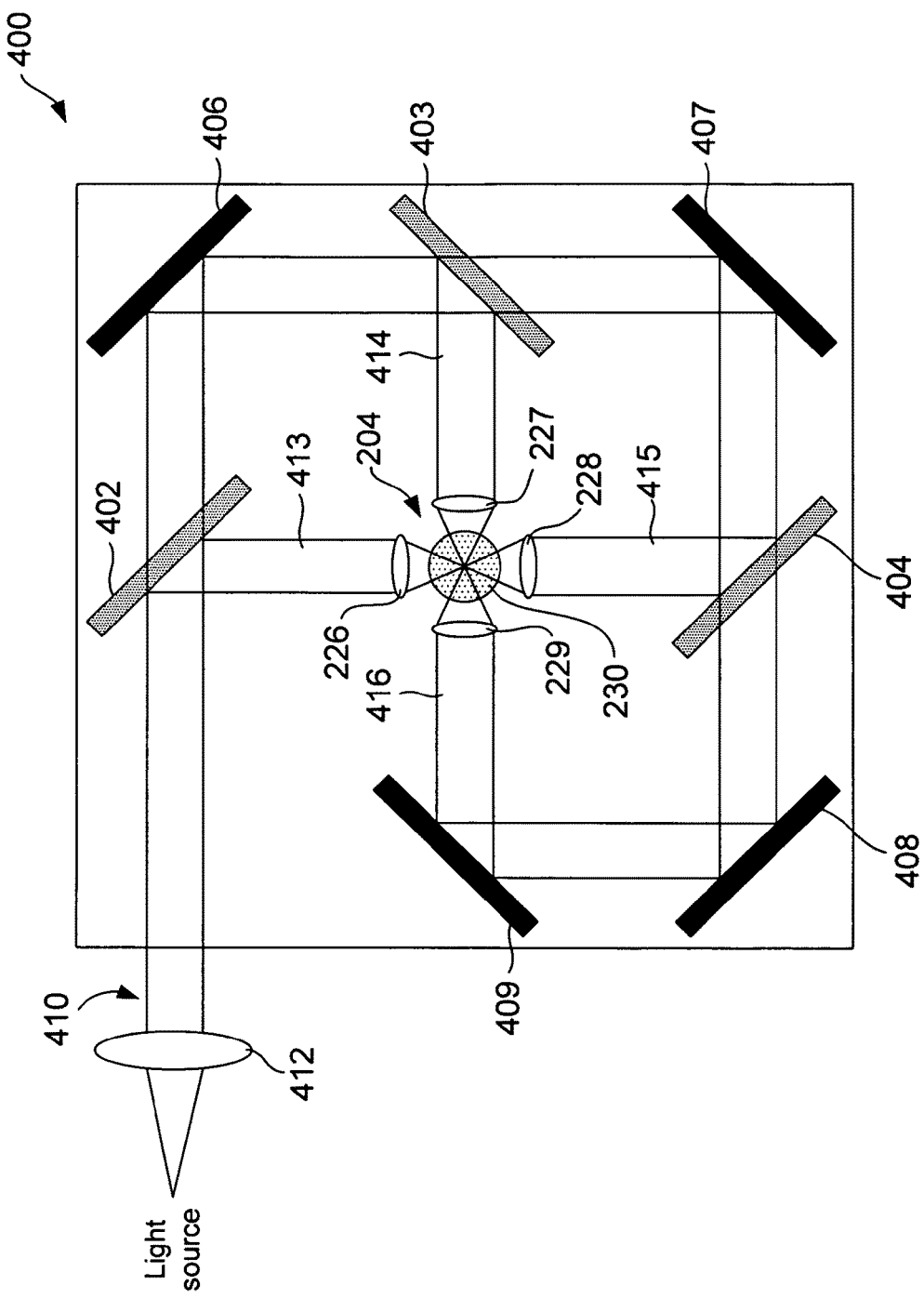
FIG. 4 shows a schematic representation of a second system for performing Raman spectroscopy configured in accordance with embodiments of the present invention.

The system 100 shown in FIG. 1 provides a general representation of systems configured in accordance with embodiments of the present invention for performing Raman spectroscopy. FIGS. 2-4 show exemplary system architectures for performing Raman spectroscopy using only four coherent beams of light focused on the surface of an analyte holder. In accordance with the general system 100, the system architectures described below can be scaled up or down and are not limited to just four beams.

Figure 2A:
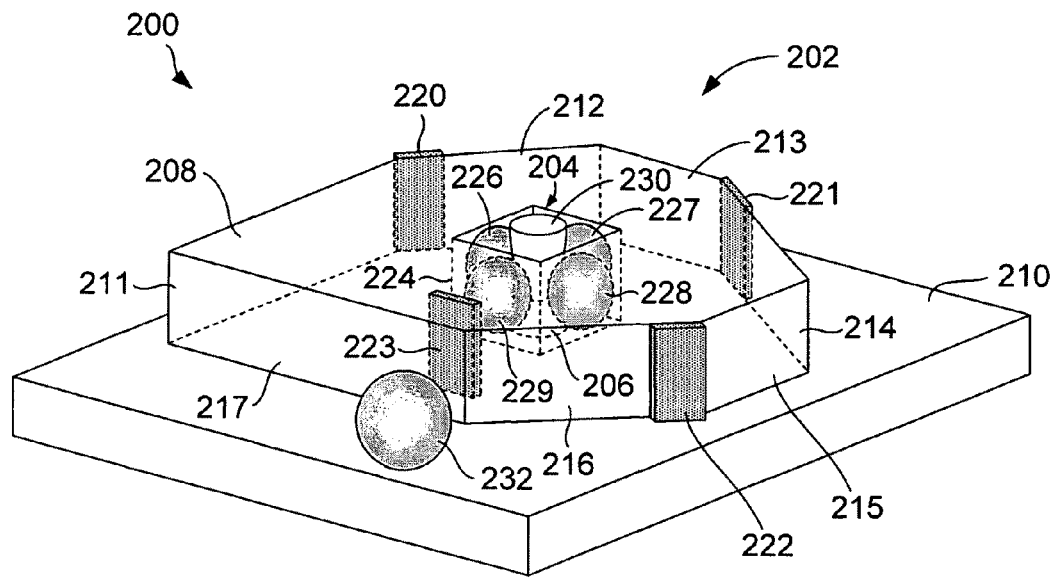
FIG. 2A show an isometric view of a first system for performing Raman spectroscopy in accordance with embodiments of the present invention.
Figure 2B:
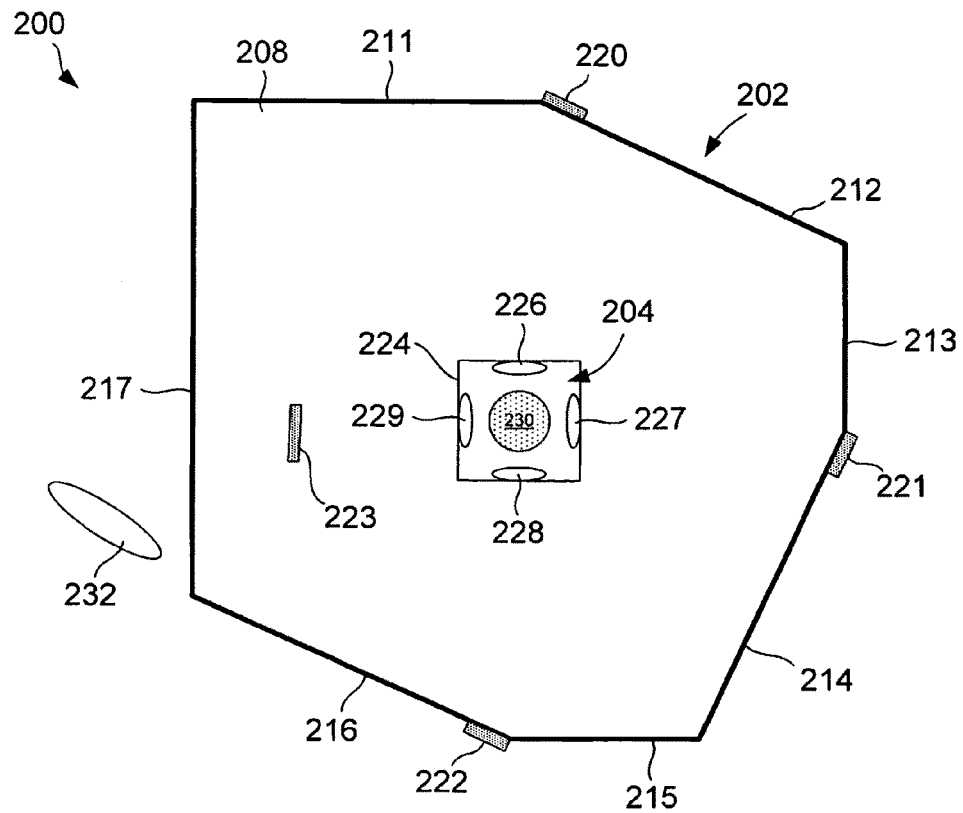
FIG. 2B shows a top-plan view of the first system for performing Raman spectroscopy in accordance with embodiments of the present invention

FIGS. 2A-2B show an isometric and a top-plan view of a first system 200 for performing Raman spectroscopy in accordance with embodiments of the present invention. As shown in FIG. 2A, the system 200 comprises a light concentrator 202, a collector 204, and an analyte holder 206. The light concentrator 202 comprises a single concentrator block 208 composed of an acrylic or other substantially transparent material disposed on a surface 210. The concentrator block 208 is configured with seven angled surfaces 211-217 directed substantially perpendicular to the surface 210. The light concentrator 202 also includes mirrors 220-222 disposed on portions of the angled surfaces 212, 214, and 216, respectively, and a mirror 223 disposed within the concentrator block 208. The collector 204 is disposed within a hollowed-out region 224 of the concentrator block 208. The collector 204 includes four lenses 226-229 and a light collimator 230 disposed on the analyte holder 206, as shown in FIG. 2A. A lens 232 is positioned outside the concentrator 202 and can be oriented to direct light output from a light source into the concentrator block 208.

FIG. 3 shows operation of the system 200 in accordance with embodiments of the present invention. A light source outputs coherent light that is collimated into an incident beam 300 directed into the concentrator block 208 toward the angled surfaces 211 and 212. As shown in FIG. 3, the representation of the incident beam 300 includes different parallel line patterns that separate four portions 301-304 of the incident beam 300. The surfaces 211-216 are angled with respect to the surface 217 and the mirrors 220-222 are disposed on portions of the surfaces 212, 214, and 216 to operate as beamsplitters that reflect each portion of the incident beam 300 toward the collector 204 as a separate beam carrying approximately ¼th of the total optical power of the incident beam 300. In particular, the portions 302-304 of the incident beam 300 are reflected off of the surface 211 toward the angled surfaces 213 and 214, and the portion 301 is reflected off of the mirror 220 toward the lens 226. The portions 303 and 304 are reflected off of the surface 213 toward the angled surfaces 215 and 216, and the portion 302 is reflected off of the mirror 221 toward the lens 227. The portion 304 is reflected off the surface 215 toward the mirror 223, and the portion 303 is reflected off of the mirror 222 toward the lens 228. The portion 304 is reflected off of the mirror 223 toward the lens 229. Each of the lenses 226-229 focuses the beams 301-304, respectively, onto a surface (not shown) of the analyte holder (not shown) disposed within the light collimator 230, and each of the beams 301-304 carries approximately ¼th of the total optical power of the incident beam 300.

As shown in FIG. 3, mirrors are not disposed on the surfaces 211, 213, and 215 to reflect the portions 302-304. Instead, the surfaces 211, 213, and 215 are angled so that the angles-of-incidence of the portions 302-304 with the surfaces 211, 213, and 215 are less than the critical angles associated with these surfaces. As a result, the portions 302-304 are reflected off of the surfaces 211, 213, and 215 due to total internal reflection. In other embodiments, mirrors can be disposed on surfaces of the concentrator block 208 where the angle-of-incidence associated with a portion of an incident beam is greater than the critical angle and it is not possible to guide the portion through the concentrator block 208 relying entirely on total internal reflection. As shown in FIGS. 2-3, a hollowed-out region houses the collector 204 and is configured as a square-shaped hole in the concentrator block 208. In other embodiments, the hollowed-out region 104 can be rectangular, circular, elliptical, or any other suitable shape for supporting the components of the collector 204. In certain embodiments, the mirrors 220-223 can be shaped to focus the beams 301-304 onto a surface of the analyte holder thereby eliminating the need for the lenses 226-229.

FIG. 4 shows a schematic representation of a second system 400 for performing Raman spectroscopy configured in accordance with embodiments of the present invention. The system 400 comprises three beamsplitters 402-404 and four mirrors 406-409. A light source outputs coherent light that is collimated into an incident beam 410 directed to the first beamsplitter 402 by the lens 412. The beamsplitters 402-404 can be separately configured in accordance with the reflectance, $R_m$, and the transmittance, $T_m$, described above with reference to FIG. 1, so that the optical power carried by each of the beams 413-416 reflected toward the collector 204 is approximately ¼th of the optical power of the incident beam 410. This can be accomplished by configuring the first beamsplitter 402 to reflect approximately ¼th of the optical power from the incident beam 410 to the lens 226, configuring the second beamsplitter 403 to reflect approximately ⅓ of the optical power carried by the beam reflected off the mirror 406 to the lens 227, and configuring the beamsplitter 404 to reflect approximately ½ of the optical power carried by the beam reflected off the mirror 407 to the lens 228. The mirror 409 can be thought of as a beamsplitter with 100% reflectance and 0% transmittance. As a result, the beams 413-416 are focused onto the surface of the analyte holder (not shown) disposed within the light collimator 230, and each beam carries approximately ¼th of the optical power of the incident beam 410.

Figure 5B:
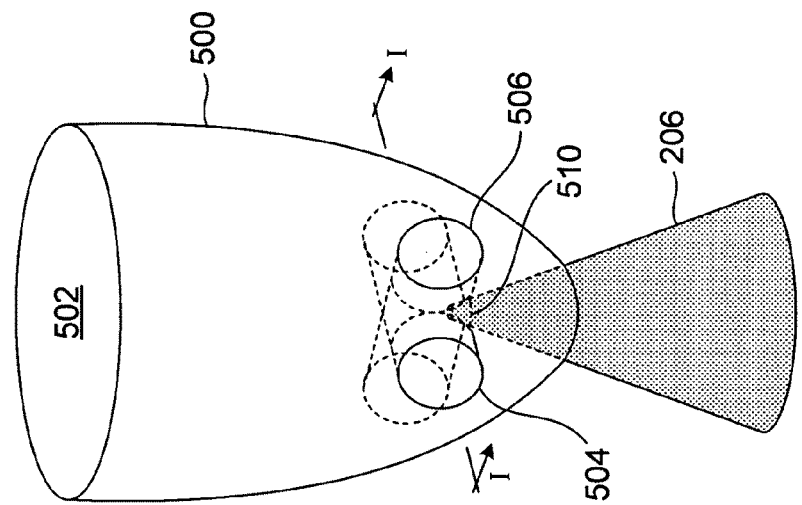
FIGS. 5A-5B show isometric views of a compound parabolic concentrator and an analyte holder configured in accordance with embodiments of the present invention.
Figure 5A:
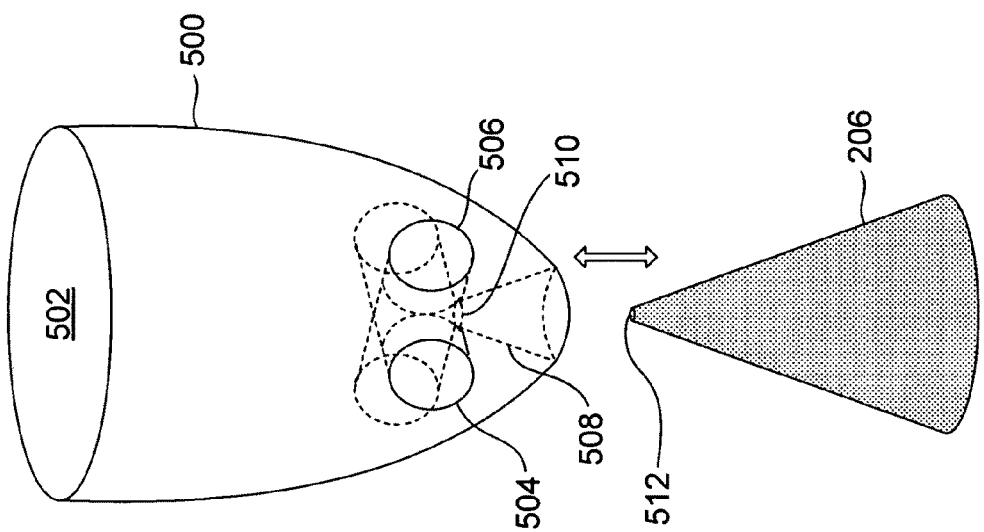

In certain embodiments, the light collimator 230 can be a compound parabolic concentrator ("CPC"). FIG. 5A shows an exploded isometric view of the CPC 500 and the analyte holder 206 configured in accordance with embodiments of the present invention. The CPC 500 comprises a broad flat surface 502 and a parabolic-shaped outer surface that curves and tapers away from the surface 502. The CPC 500 includes two intersecting cylindrical-shaped holes 504 and 506 directed substantially parallel to the surface 502 and a cone-shaped hole 508 that tapers toward and includes an opening 510 into the intersecting region of the two holes 504 and 506. FIG. 5A also reveals the analyte holder 206 as cone-shaped with a flattened tip at the tapered end that supports a surface 512. In other embodiments, the holes 504 and 506 can have square, rectangular, elliptical, irregular-shaped cross sections, or have any other suitably-shaped cross section. FIG. 5B shows the tapered portion of the analyte holder 206 inserted into the cone-shaped hole 508 of the CPC 500 in accordance with embodiments of the present invention. FIG. 5B reveals that a portion of the analyte holder 206 and the surface 512 extend into the intersecting region of the holes 504-506.

FIGS. 6A-6C show three cross-sectional views of the analyte holder 206 inserted into the CPC 500 along a line I-I, shown in FIG. 5B, in accordance with embodiments of the present invention. In all three views, the surface 512 of the analyte holder 206 is located within the intersecting region of the cylindrical holes 504 and 506. As shown in FIG. 6A, the analyte holder 206 is configured to include a channel 602 that opens onto the surface 512. The channel 602 is used to deliver an analyte to the surface 512 through the analyte holder 206. In other embodiments, as shown in FIG. 6B, an analyte can be delivered to the surface 512 via a capillary tube 604 inserted into one of the cylindrical holes 504 and 506. In still other embodiments, as shown in FIG. 6C, the CPC 500 can be configured to include a hole 606 through which a capillary tube 608 is inserted to deliver an analyte to the surface 512.

In other embodiments, the light collimator 230 can be a hollowed-out reflector having substantially the same parabolic shape and holes 504, 506, and 508 as the CPC 500 and can also be used to collimate light emitted from an analyte in proximity to or absorbed on the surface 512.

The surface 512 is disposed on a flattened-tip portion of the analyte holder 206 and can be composed of Au, Ag, Cu, a semiconductor, or any other suitable material for retaining an analyte and enabling formation of surface plasmons on the surface 512. In order to enhance the electromagnetic field interaction with an analyte, the surface 512 can also be configured with features, such as arrays of nanowires, tapered nanowires, cones, and depressions in the surface 512.

Figure 7:
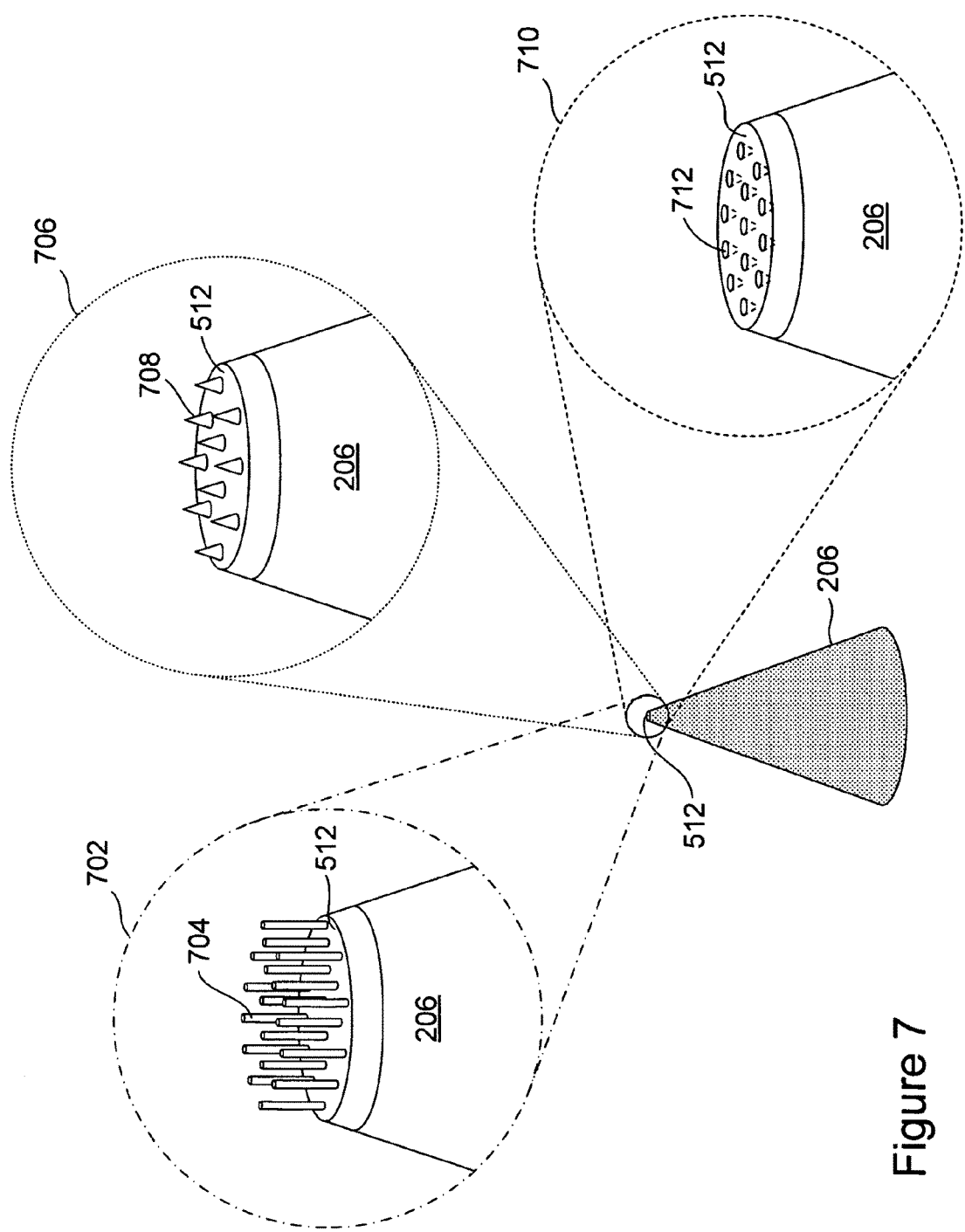
FIG. 7 shows magnified views of three different kinds of features that can be formed on a surface of an analyte holder in accordance with embodiments of the present invention.

FIG. 7 shows isometric magnified views of three different kinds of features that can be formed on or within the surface 512 in accordance with embodiments of the present invention. Magnified view 702 reveals nanowires, such as nanowire 704, extending substantially perpendicular to and disposed on the surface 512. The nanowires can be formed using a vapor-liquid-solid ("VLS") or vapor-solid-solid ("VSS") growth mechanism. When closely spaced nanowires are needed, a diblock copolymer can be used to form a regular pattern of holes on the surface 512 through which seed particles can be deposited using an electroless or other deposition process. When larger spacing is needed, nanoimprint lithography can be used to form a pattern on the surface 512 into which the seed particles can be deposited. The seed particles are composed of a catalyst material such as gold or titanium. After the seed particles are deposited, the analyte holder 206 is placed in an oven and heated to temperatures typically ranging between about 250° C. to about 1000° C. Precursor gasses including elements or compounds that will be used to form the nanowires are introduced into the chamber. The particles of the catalyst material cause the precursor gasses to at least partially decompose into their respective elements, some of which are transported onto or through the particles of the catalyst material and deposited on the underlying surface. Continued supply of the vapor-phase reactants results in supersaturation of the catalyst material, which eventually causes precipitation of excess solid-phase material forming the nanowires beneath the seed particles, which can be in either the liquid state or solid state during nanowire growth. Nanowires grow as the process continues with the catalyst particle remaining on the tip or end of the nanowires. Nanowires can also be formed by physical vapor deposition or by surface atom migration. Magnified view 706 reveals cones, such as cone 708, extending above the surface 512. The cones and tapered nanowires can be formed using the same VLS and VSS methods for forming a nanowire, but the shape is tapered by varying the ratio of precursor gases to control the rate of catalyzed deposition to that of uncatalyzed deposition during nanowire growth. Magnified view 710 reveals depressions, such as depression 712, formed in the surface 512. A pattern of depressions can be formed using reactive ion etching, focused ion beam milling, possibly combined with nanoimprint, electron-beam, or conventional lithography, or any other suitable method for forming depressions in the surface 512. In other embodiments, the features can be pyramids or other structures formed on or within the surface 512. The features formed on the surface 512, such as the nanowires and cones, can be composed of elemental semiconductors, such as silicon and germanium, or composed of compound III-V and II-IV semiconductors.

In certain embodiments, the analyte holder 206 can have a base diameter of approximately 10 mm and the surface 512 can have a diameter of approximately 1 mm. The features formed on or within the surface 512 can be spaced by 10s to 100s of nanometers and the diameters of the nanowires, cones, and depressions can be 10s of nanometers.

Figure 8:
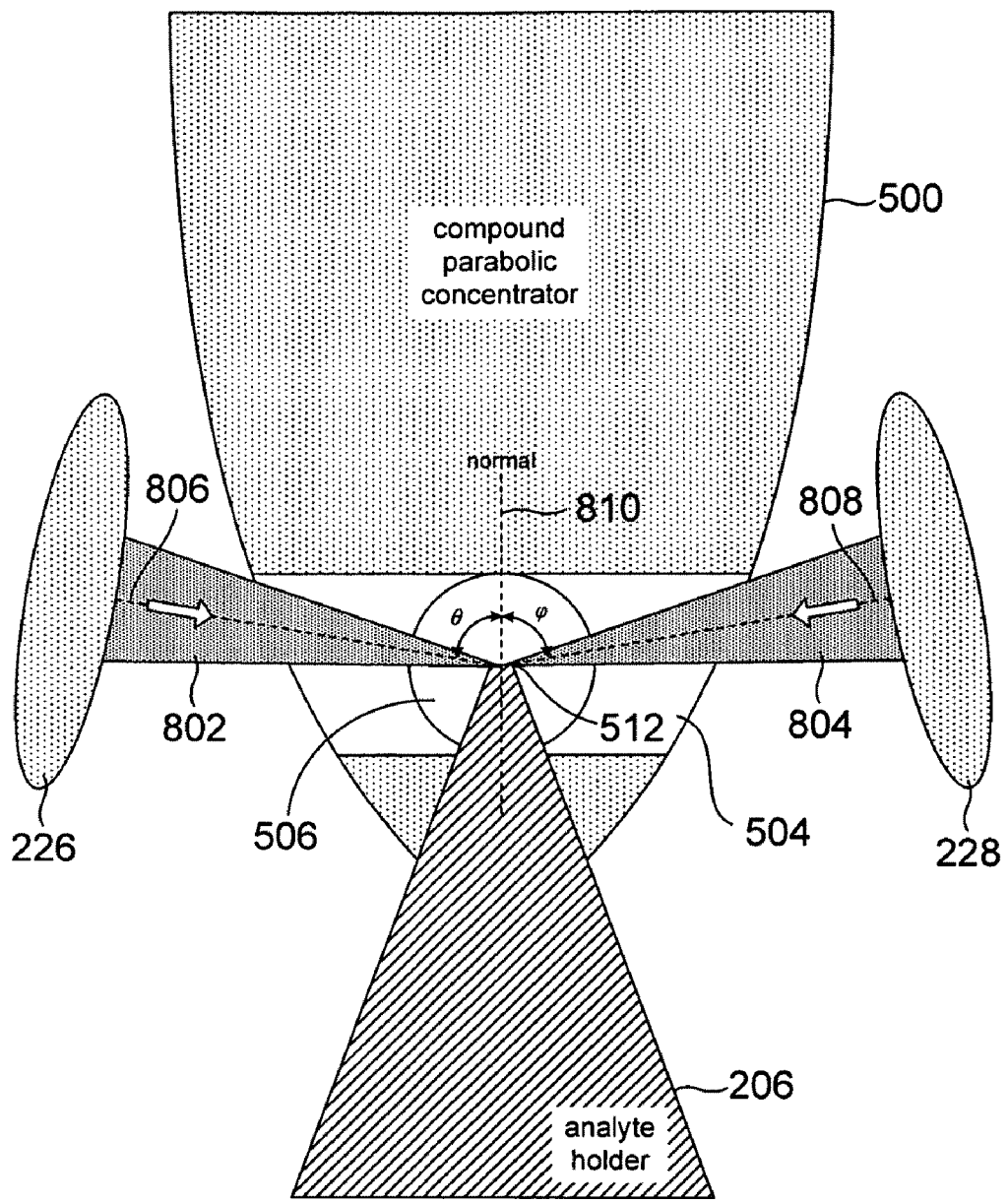
FIG. 8 shows a cross-sectional view of a compound parabolic concentrator and an analyte holder along the line I-I, shown in FIG. 5B, representing different angles at which the focused beams can intersect at a surface of the analyte holder in accordance with embodiments of the present invention.

The angles at which the intersecting beams are incident on the surface 512 determine where the electric field associated surface plasmons formed on the surface 512 is strongest. Thus embodiments of the present invention include enabling the lens 226-229 to be oriented to focus the intersecting beams with different angles-of-incidence on the surface 512. FIG. 8 shows a cross-sectional view of the CPC 500 and the analyte holder 206 along the line I-I, shown in FIG. 5B, representing different angles at which the focused beams can intersect at the surface 512 of the analyte holder 206 in accordance with embodiments of the present invention. In FIG. 8, only two of the four cone-shaped focused beams 802 and 804 intersecting on the surface are represented, and dashed-lines 806 and 808 represent the central axes of the focused beams 802 and 804, respectively. FIG. 8 includes a surface normal 810, which is a vector extending perpendicular to the surface 512. FIG. 8 shows the lenses 226 and 228 positioned so that the central axes 806 and 808 of the focused beams 802 and 804 intersect on the surface 512 with angles-of-incidence represented by $\theta$ and $\phi$, respectively. The angle-of-incidence is the angle between the central axes 806 and 808 of the focused beams 802 and 804 and the normal 810.

Figure 9B:
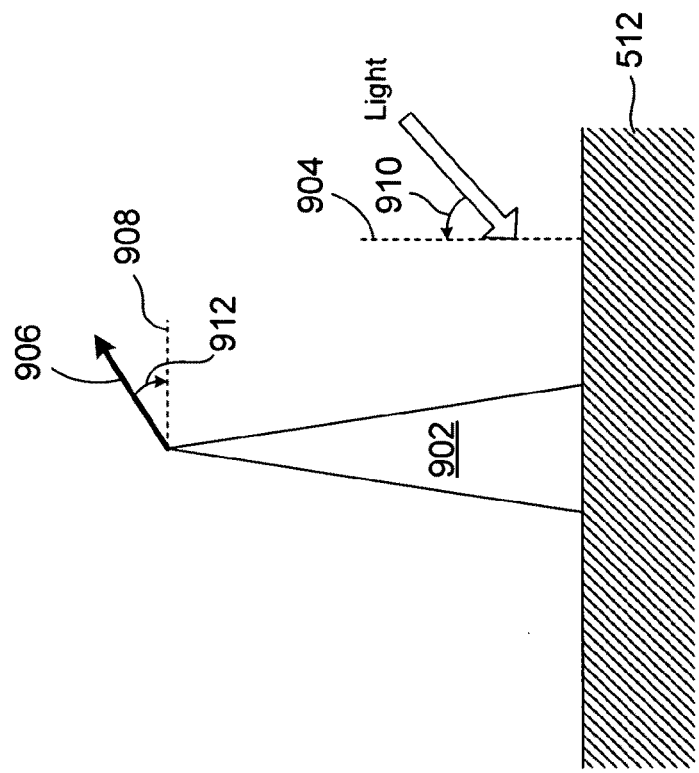
FIGS. 9A-9B show how direction and position of an electric field emanating from a tapered nanowire changes as a result of light striking the tapered nanowire from different directions in accordance with embodiments of the present invention.
Figure 9A:
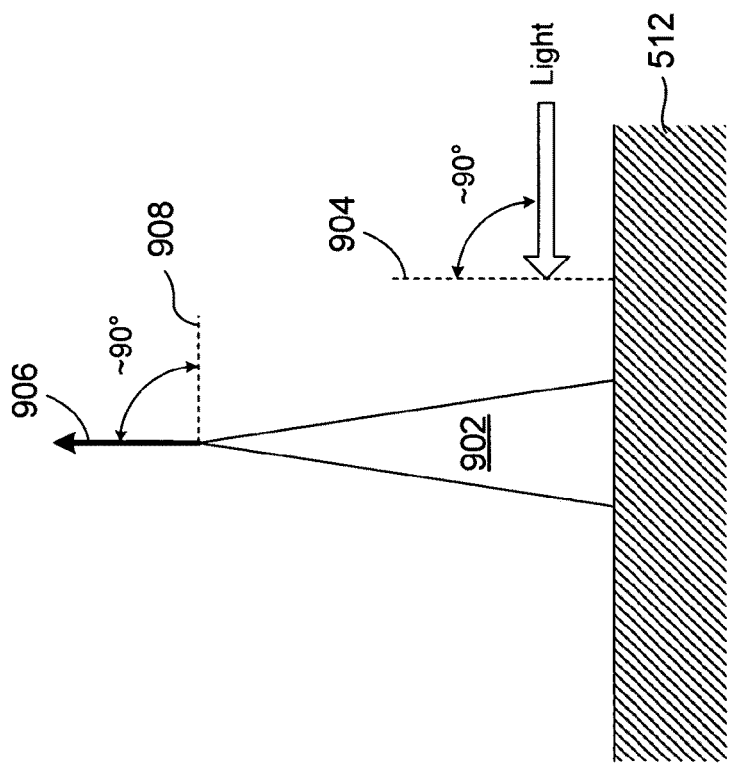

In certain embodiments, the angles-of-incidence can all be approximately 90°. In other embodiments, the angles-of-incidence can be approximately the same or any combination of different angles. The angle-of-incidence can be tuned to change the direction of the electric field produced by surface plasmons formed on features of the surface 512. FIGS. 9A-9B show cross-sectional views of a tapered nanowire 902 extending above a portion of the surface 512 in accordance with embodiments of the present invention. FIGS. 9A-9B reveal how the direction of an electric field emanating near the tip of the tapered nanowire 902 changes as a result of the direction light strikes the tapered nanowire 902. As shown in FIG. 9A, when light strikes the tapered nanowire 902 with an angle-of-incident approaching 90° to the surface 512 normal 904 or substantially parallel to the surface 512, the direction of the electric field oscillations, represented by directional arrow 906, are directed approximately 90° to the planar direction 908 of the surface 512. In addition, the electric field is concentrated near the tip of the tapered nanowire 902. On the other hand, as shown in FIG. 9B, as the angle-of-incidence of light striking the tapered nanowire 902 approaches 0° to the surface 512 normal 904 or substantially perpendicular to the surface 512, as indicated by directional arrow 910, the direction of the electric field oscillations approaches the planar direction 908, as indicated by directional arrow 912, and the electric field remains concentrated near the tip of the tapered nanowire 902.

Figure 10:
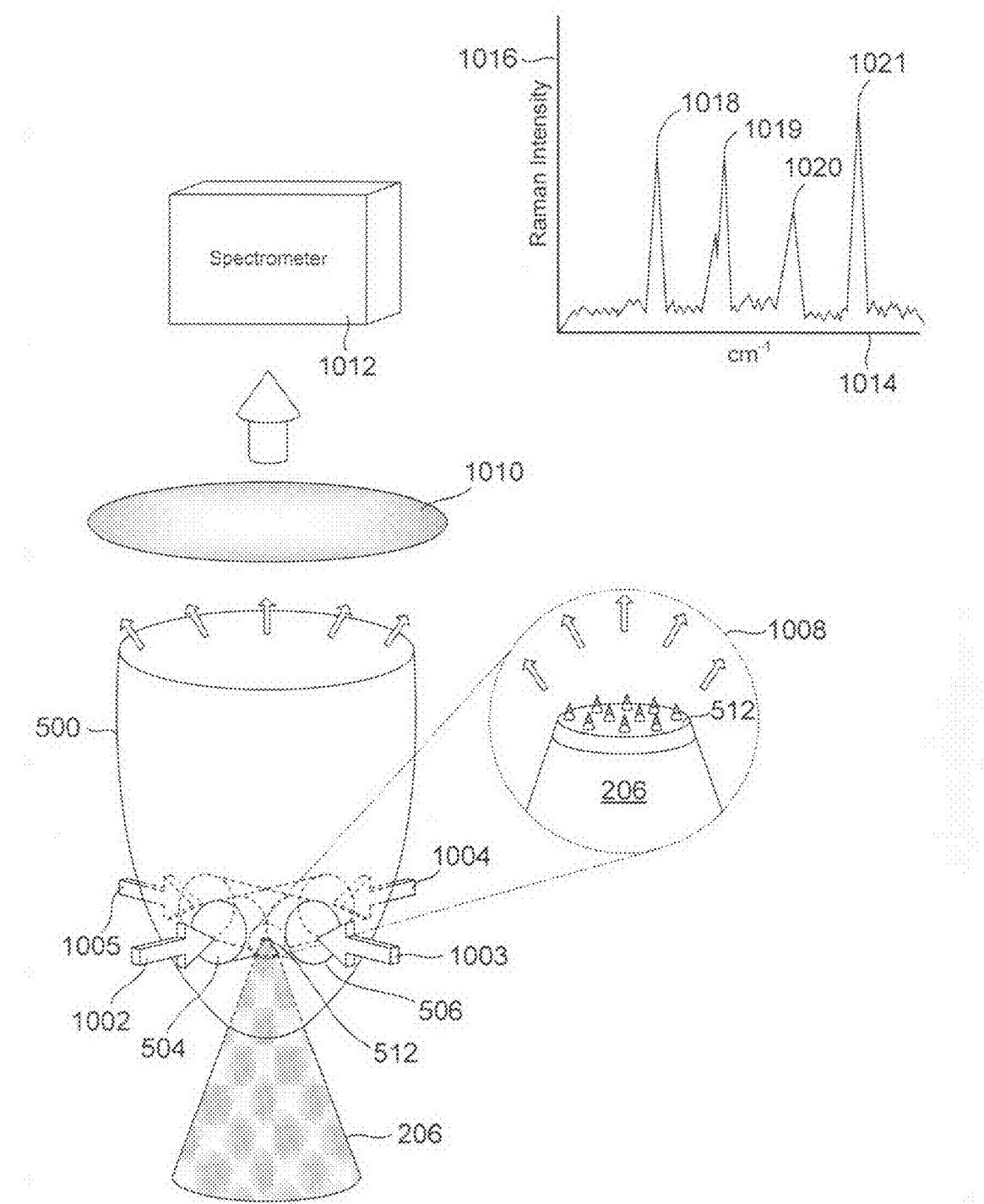
FIG. 10 shows operation of a compound parabolic concentrator and an analyte holder in accordance with embodiments of the present invention.

FIG. 10 shows operation of the CPC 500 and the analyte holder 206 in accordance with embodiments of the present invention. As shown in FIG. 10, directional arrows 1002-1005 represent light focused onto the surface 512 as described above with reference to FIG. 8. The wavelength of light is selected to interact with an analyte disposed on the surface 512 and to interact with the surface 512 to form surface plasmons. An increase in intensity of the Raman spectrum emitted from analytes retained on the surface 512 occurs because of an enhancement in the electric field produced by surface plasmons forming on features of the surface 512. The focused beams constructively interfere at the surface, produce interference fringes with a peak intensity proportional to the number of beams striking the surface 512, and have a periodicity of $\lambda/2$. When the focused beams of light 1002-1005 strike the surface 512, localized surface plasmons are excited, which in turn generate electric fields. The electric field enhancement is greatest when the plasmon frequency is in resonance with the frequency corresponding to the wavelength of the focused beams. In order for efficient Raman scattering to occur, the plasmon oscillations are substantially perpendicular to the surface 512. Features formed on the surface 512, such as the tapered nanowires shown in magnified view 1008 and in FIGS. 9A-9B, provide an area on which these localized collective oscillations can take place. When the beams focused on the surface 512 have angles-of-incidence of approximately 90° to the surface 514 normal, enhancement of the electric field is greatest at the tips of the features. For example, the tips of the cones shown in magnified view 1008 are shaded in order to represent the enhanced electric field formed at the tips of the cones. The electric field enhancement magnifies the intensity of incident light and excites the Raman modes of the analyte molecules, and thereby increases the Raman scattering. The CPC 500 gathers and collimates at least a portion of the Raman scattered light emitted from the analyte. The collimated light exits the CPC 500 through the surface 502 and a lens 1010 can be used to further focus the beam onto detectors of a spectrometer 1012. FIG. 10 also includes an exemplary plot of a Raman spectrum. The plot comprises a horizontal wavenumber axis 1014, a vertical Raman intensity axis 1016, and a representation of the Raman spectrum comprising four peaks 1018-1021. Each peak is associated with a particular wavenumber that can be used to identify the chemical bonds of an analyte retained by the surface 512.

When the analyte comprises charged molecules, the molecules are attracted by the electric field to the features. Uncharged molecules with a built-in dipole moment may also be attached to the features, and uncharged molecules without a built-in dipole moment may still be attracted to the features because the electric field can induce a dipole moment in certain uncharged molecules.

The materials selected for the substrate 512 can be determined by the plasmon resonance frequency. For example, light with wavelengths in the visible and near-infrared portions of the electromagnetic spectrum can be used to excite Raman modes. Therefore, the surface 512 can be composed of Ag or Au, because the surface plasmons formed on surfaces composed of these materials have resonance frequencies that fall within the wavelength ranges of visible and near-infrared portions of the electromagnetic spectrum, providing maximal enhancement for visible and near-infrared light. The surface 512 can also be composed of Cu, which is another suitable metal whose absorption spectrum falls within the range acceptable for SERS.

In other embodiments, rather than configuring the tip of the analyte holder 206 with a surface 512 having a number of features, the tip of the analyte holder 206 can be comprised of single nano-scale tip. The beams of light could then be focused on the tip and the system 100, 200, and 400 operated as described above. In other embodiments, the collector can be configured with reflectors that recycle and refocus specular reflection off of the surface back to the surface to increase interaction with the analyte and further enhance the electric field.

The foregoing description, for purposes of explanation, used specific nomenclature to provide a thorough understanding of the invention. However, it will be apparent to one skilled in the art that the specific details are not required in order to practice the invention. The foregoing descriptions of specific embodiments of the present invention are presented for purposes of illustration and description. They are not intended to be exhaustive of or to limit the invention to the precise forms disclosed. Obviously, many modifications and variations are possible in view of the above teachings. The embodiments are shown and described in order to best explain the principles of the invention and its practical applications, to thereby enable others skilled in the art to best utilize the invention and various embodiments with various modifications as are suited to the particular use contemplated. It is intended that the scope of the invention be defined by the following claims and their equivalents:

The invention claimed is:

1. A system for performing Raman spectroscopy comprising:
   an analyte holder having a surface to retain an analyte;
   a light concentrator to split an incident beam of light into two or more beams that lie within a plane and direct the two or more beams to substantially intersect at the analyte surface; and
   a collector to focus each of the two or more beams onto the analyte surface, collect Raman scattered light emitted from the analyte, and direct the Raman scattered light away from the analyte surface approximately perpendicular to the plane.

2. The system of claim 1 further comprising:
   a lens to receive and focus the Raman scattered light; and
   a spectrometer to receive the Raman scattered light and measure a Raman spectrum associated with the analyte.

3. The system of claim 1 wherein the light concentrator further comprises a concentrator block with multiple surfaces angled to split the incident beam of light into the two or more beams directed to the analyte surface.

4. The system of claim 3 wherein the concentrator block further comprises mirrors disposed on selected surfaces to direct each of the two or more beams to intersect at the surface.

5. The system of claim 1 wherein the light concentrator further comprises:
   two or more beamsplitters to split the incident beam of the light into the two or more beams directed to the analyte holder surface; and
   mirrors positioned to receive the transmitted beam of light and direct the transmitted beam of light to the analyte surface.

6. The system of claim 1 wherein the collector further comprises:
   a light collimator including a first opening to receive the analyte holder and two or more openings that intersect the first opening and receive the two or more beams directed by the light concentrator to intersect at the analyte holder surface; and
   two or more lenses, each lens to receive and focus one of the two or more beams onto the surface.

7. The system of claim 6 wherein the light collimator further comprises one of:
   a compound parabolic concentrator; and
   hollowed-out reflector.

8. The system of claim 1 wherein the analytic holder further comprises a cone-shaped holder having a flattened tip located at the tapered end of the cone-shaped holder, the flatted tip to support the surface.

9. The system of claim 1 wherein the analyte holder further comprises a channel through which the analyte can be injected onto the surface.

10. The system of claim 1 wherein the surface further comprises one of: gold, silver, copper, silicon, germanium, a compound semiconductor to retain an analyte and enable formation of surface plasmons.

11. The system of claim 1 further comprising features, wherein the features are one of: nanowires, tapered nanowires, cones, and depressions.

12. The system of claim 1 wherein the surface further comprises a single nano-tip to retain the analyte.

13. A method for performing Raman spectroscopy comprising:
   splitting an incident coherent beam of light into two or more coherent beams of light that lie within a plane, each of which has approximately the same optical power;
   directing the two or more coherent beams of light to intersect at a surface of an analyte holder;
   focusing each of the two or more coherent beams onto the surface of the analyte holder; and
   directing Raman scattered light emitted from an analyte retained on the surface away from the surface toward a spectrometer, the Raman scattered light directed perpendicular to the plane.

14. The method of claim 13 wherein splitting the coherent beam of light into two or more beams further comprises passing the incident coherent beam of light through a concentrator block to reflect portions of the incident beam toward the surface of the analyte holder, wherein the reflected portions have approximately the same optical power.

15. The method of claim 13 wherein splitting the coherent beam of light into two or more beams further comprises passing the incident coherent beam of light through two or more beamsplitters, wherein each beamsplitter reflects a portion of the incident beam of light so that each portion has approximately the same optical power.

16. The method of claim 13 wherein directing the two or more coherent beams of light to intersect at the surface further comprises reflecting the coherent beams toward the surface.

17. The method of claim 13 wherein focusing each of the two or more coherent beams onto the surface of the analyte further comprises passing each of the two or more coherent beams of light through a corresponding lens configured and positioned to focus the beam onto the surface.

18. The method of claim 13 wherein focusing each of the two or more coherent beams onto the surface of the analyte further comprises
   constructively interfering electromagnetic waves of the two or more coherent beams; and
   forming surface plasmons on the surface of the analyte holder to enhance electric field interaction with the analyte.

19. The method of claim 13 wherein directing scattered light emitted from the analyte further comprises:
   gathering the Raman scattered light in a light collimator; and
   passing the Raman scattered light output from the light collimator through a lens to focus the light onto a detector portion of the spectrometer.

20. The method of claim 19 wherein the light collimator further comprises one of:
   a compound parabolic concentrator; and
   a hollowed reflector.

* * * * *

UNITED STATES PATENT AND TRADEMARK OFFICE
CERTIFICATE OF CORRECTION

| | | |
|---|---|---|
| PATENT NO. | : 8,054,461 B2 | Page 1 of 1 |
| APPLICATION NO. | : 12/286490 | |
| DATED | : November 8, 2011 | |
| INVENTOR(S) | : Huei Pei Kuo et al. | |

It is certified that error appears in the above-identified patent and that said Letters Patent is hereby corrected as shown below:

In column 9, line 29, in Claim 5, delete "of the" and insert -- of --, therefor.

In column 9, line 48, in Claim 8, delete "analytic" and insert -- analyte --, therefor.

In column 9, line 56, in Claim 10, delete "a" and insert -- or a --, therefor.

Signed and Sealed this
Seventh Day of August, 2012

David J. Kappos
*Director of the United States Patent and Trademark Office*